US009717595B2

(12) United States Patent
Costello et al.

(10) Patent No.: US 9,717,595 B2
(45) Date of Patent: Aug. 1, 2017

(54) TRANS-AORTIC DELIVERY SYSTEM WITH CONTAINMENT CAPSULE CENTERING DEVICE

(75) Inventors: Declan Costello, Ballybrit (IE); Patrick Griffin, Ballybrit (IE); John Gallagher, Ballybrit (IE); Gavin Kenny, Ballybrit (IE); Edmond Sheahan, Ballybrit (IE)

(73) Assignee: Medtronic Vascular Galway, Ballybrit, Galway (IE)

( * ) Notice: Subject to any disclaimer, the term of this patent is extended or adjusted under 35 U.S.C. 154(b) by 900 days.

(21) Appl. No.: 13/604,150

(22) Filed: Sep. 5, 2012

(65) Prior Publication Data

US 2014/0067050 A1 Mar. 6, 2014

(51) Int. Cl.
*A61F 2/24* (2006.01)
*A61F 2/962* (2013.01)
*A61F 2/95* (2013.01)

(52) U.S. Cl.
CPC ............ *A61F 2/2436* (2013.01); *A61F 2/962* (2013.01); *A61F 2002/9517* (2013.01)

(58) Field of Classification Search
CPC ........ A61F 2/2436; A61F 2/962; A61F 2/966; A61F 2002/9665; A61F 2/2427
See application file for complete search history.

(56) References Cited

U.S. PATENT DOCUMENTS 7,914,569 B2 3/2011 Nguyen et al.
8,016,877 B2 9/2011 Seguin et al.
2011/0282425 A1* 11/2011 Dwork ...................... A61F 2/95 623/1.11
2011/0301685 A1 12/2011 Kao
2013/0274870 A1* 10/2013 Lombardi ............. A61F 2/2418 623/2.11

FOREIGN PATENT DOCUMENTS

| | | |
|---|---|---|
| WO | WO2009/091509 | 7/2009 |
| WO | WO2010/045297 | 4/2010 |
| WO | WO2011/094527 | 8/2011 |
| WO | WO2011/144351 | 11/2011 |
| WO | WO2012/038550 | 3/2012 |

OTHER PUBLICATIONS

PCT/US2013/056890, PCT International Search Report, mailed Dec. 19, 2013, 6pages.

* cited by examiner

*Primary Examiner* — Thomas McEvoy

(57) ABSTRACT

Heart valve delivery systems and methods of delivering and implanting heart valves using delivery catheters are disclosed. The delivery systems can include a handle assembly which can include a first control mechanism, a second control mechanism, and a decoupling mechanism. The delivery systems can also include a delivery catheter extending from the handle assembly. The delivery catheter can include an outer shaft, which can be controlled by the first control mechanism; a prosthesis containing capsule comprising a proximal capsule portion connected to the outer shaft, and a distal capsule portion releasably coupled to the proximal capsule portion. After deploying a valve prosthesis, the capsule can be closed by activating the decoupling mechanism in the handle to rapidly close the distal and proximal capsule portions together. The delivery system can also include a centering element to guide the distal and proximal capsule portions together.

10 Claims, 12 Drawing Sheets

TRANS-AORTIC DELIVERY SYSTEM WITH CONTAINMENT CAPSULE CENTERING DEVICE

BACKGROUND

Field

The present disclosure relates to systems for delivering a prosthesis to a desired location in the body of a patient and methods for delivering and implanting a prosthesis. More particularly, the present disclosure relates to prosthetic valve delivery systems for deploying a heart valve prosthesis within a body lumen and to methods of delivering such a prosthesis to a desired location in the body.

Background

Currently, replacement of a deficient cardiac valve is often performed by placing the patient under extracorporeal circulation, temporarily stopping the heart, opening the thorax (e.g., by a sternotomy), surgically opening the heart, excising the deficient valve, and then implanting a prosthetic valve in its place. This procedure generally requires prolonged patient hospitalization, as well as extensive and often painful recovery.

Recently, minimally invasive approaches have been developed to facilitate catheter-based implantation of valve prostheses in the beating heart, intending to obviate the need for the classic sternotomy and cardiopulmonary bypass. For example, U.S. Pat. No. 8,016,877 to Seguin et al. illustrates a technique and a device for replacing a deficient heart valve by percutaneous route. An expandable prosthetic valve can be compressed about a catheter, inserted inside a body lumen, such as the femoral artery, and delivered to a desired location in the heart. Additionally, U.S. Pat. No. 7,914,569 to Nguyen et al. discloses advancing a catheter containing a prosthesis in a retrograde manner through the femoral artery and into the descending aorta, over the aortic arch, through the ascending aorta and inside the defective aortic valve. This procedure can be assisted by fluoroscopic guidance. Once the position of the catheter containing the prosthesis is confirmed, a sheath containing the prosthesis can be moved proximally, allowing the valve prosthesis to self-expand.

Other techniques for delivering prosthetic heart valves via a catheter include transapical and trans-aortic approaches for aortic valve replacement, typically involving the use of an introducer port, i.e., a large-bore overtube, of a trocar. A crimped, framed valve prosthesis reversibly coupled to a delivery catheter can be transcatheterally advanced toward the native valve, where it can either be deployed using a balloon catheter, or, alternatively, using a self-expandable system.

With regard to the structure of the heart valve prosthesis itself, U.S. Pat. No. 7,914,569 to Nguyen et al. describes an example prosthesis for percutaneous transluminal delivery, and is incorporated by reference herein in its entirety. The heart valve prosthesis can have a self-expanding multi-level frame that supports a valve body with a skirt and plurality of leaflets. The frame can be contracted during percutaneous transluminal delivery and expanded to an hourglass shape upon deployment within the native heart valve.

BRIEF SUMMARY

The present disclosure describes delivery systems for implanting a heart valve prosthesis through a trans-aortic pathway. By directly accessing the aorta, it is possible to accurately implant a prosthetic valve without the need for cardiopulmonary bypass, although the disclosed delivery systems can also be used with cardiopulmonary bypass. Furthermore, the delivery systems disclosed herein can allow for quick and accurate retraction of a distal portion of the capsule member used to contain the valve prosthesis. It is understood that while the disclosure refers specifically to a trans-aortic procedure, the delivery systems and methods disclosed herein can also be used for any access route, vessel or location within the heart and vasculature.

In certain embodiments, the delivery systems can include a handle assembly which can include a first control mechanism, a second control mechanism, and a decoupling mechanism. The delivery systems can also include a delivery catheter extending from the handle assembly. The delivery catheter can include an outer shaft, which can be controlled by the first control mechanism, and a prosthesis containing capsule comprising a proximal capsule portion connected to the outer shaft and a distal capsule portion releasably coupled to the proximal capsule portion. The capsule can also include a distal tip and a prosthesis containment sleeve. The delivery catheter can also include an intermediate shaft having a prosthesis retainer located at its distal end, and an inner shaft which can be controlled by the second control mechanism and can be connected to the distal capsule portion. In certain embodiments, the delivery system can also include a safety mechanism, which can be connected to the first control mechanism, and configured to prevent proximal retraction of the outer shaft beyond a predetermined distance. In certain embodiments, the delivery system can also include a capsule centering element such as, but not limited to, a self-expanding frame, a self-expanding funnel, or a centering shaft.

Also disclosed herein are catheter tips, which can include a proximal capsule portion and a distal capsule portion releasably coupled to the proximal capsule portion. The distal capsule portion can include a distal tip, connected to an inner shaft of the catheter, and a prosthesis containment sleeve. The catheter tip can also include an intermediate shaft having a prosthesis retainer located at a distal end. In certain embodiments, the catheter tip can include a centering shaft having a tapered distal nose and configured to move axially along the intermediate shaft. In certain embodiments the catheter tip can include a capsule centering element attached to the intermediate shaft, located proximally from the prosthesis retainer and configured to guide the distal capsule portion and the proximal capsule portion back together after separating to deploy the valve prosthesis.

In order to deliver the prosthesis, the delivery system can be introduced into a patient's aorta and the delivery catheter can be advanced within the aorta to a deployment location. The first control mechanism can be activated to proximally retract the outer shaft and proximal capsule portion, and the second control mechanism can be activated to distally advance the distal capsule portion to release the valve prosthesis. The capsule can be closed by activating a decoupling mechanism to close the distal capsule portion and proximal capsule portion together. The delivery system can then be retracted proximally through the deployed valve prosthesis and removed from the body.

BRIEF DESCRIPTION OF THE DRAWINGS

The accompanying figures, which are incorporated herein, form part of the specification and illustrate embodiments of prosthetic valve delivery systems and methods of delivering a valve prosthesis to a desired location in a body of a patient. Together with the description, the figures further serve to explain the principles of and allow for the making and using of the prosthetic valve delivery systems and methods described herein. These figures are intended to be illustrative, not limiting. Although the disclosure is generally described in the context of these embodiments, it should be understood that it is not intended to limit the scope of the disclosure to these particular embodiments. In the drawings, like reference numbers indicate identical or functionally similar elements.

DETAILED DESCRIPTION

Figure 1:
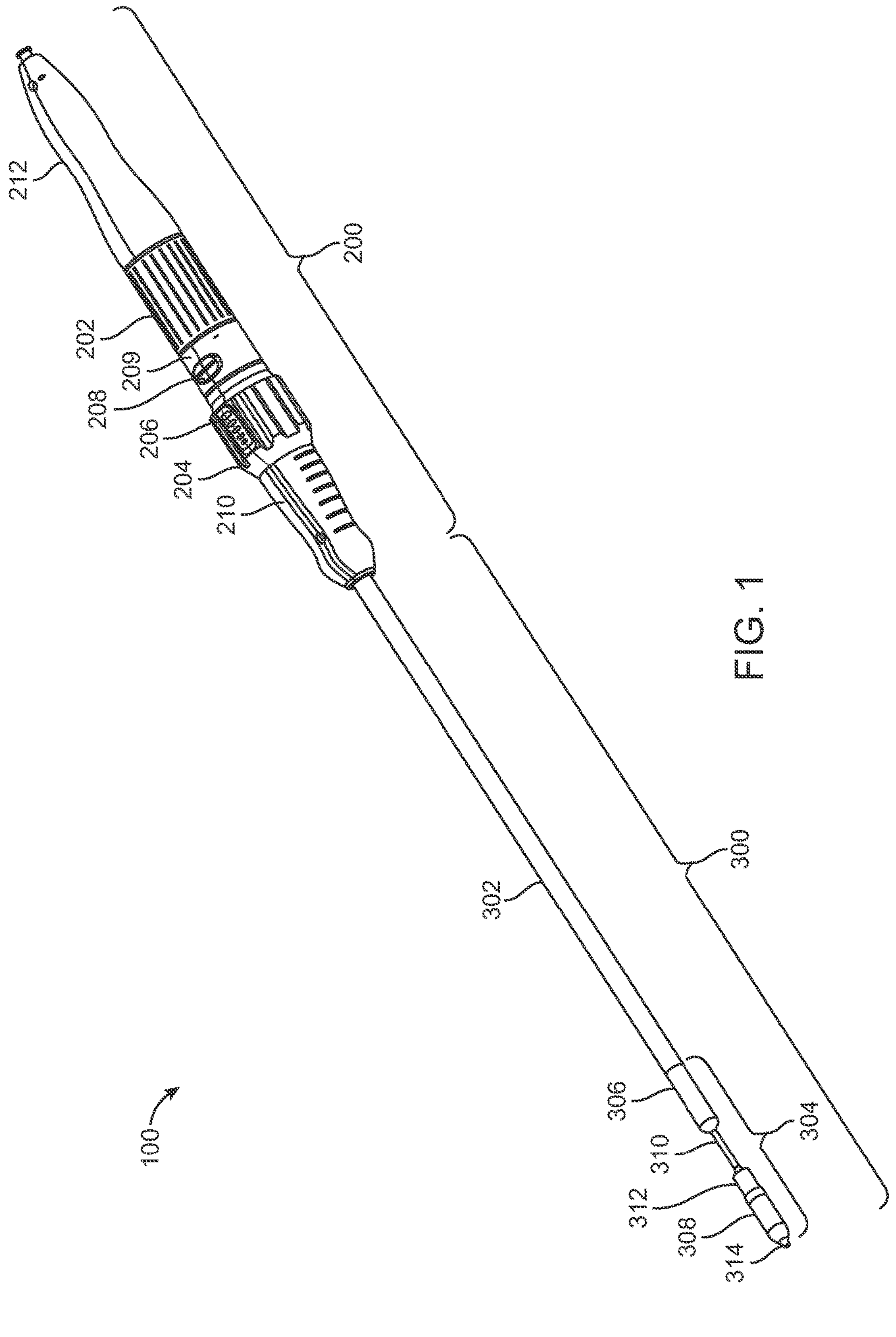
FIG. 1 illustrates a delivery system, according to an embodiment.

While the disclosure refers to illustrative embodiments for particular applications, it should be understood that the disclosure is not limited thereto. Modifications can be made to the embodiments described herein without departing from the spirit and scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The delivery systems disclosed herein can include a moldable handle capable of translating linear relative movement between multiple shafts simultaneously to deliver a valve prosthesis. The delivery systems can include a two-part prosthesis containment capsule which can maintain a compressible interference fit, mitigating risks associated with snagging during retraction of the delivery system. The delivery system handle can be reversibly decoupled, allowing for rapid closure of the prosthesis containment capsule after delivery of the prosthesis. The decoupling mechanism can be user operated and can include a safety feature to prevent premature actuation.

The delivery system can also include a safety stop feature, which can permit only partial deployment of the valve prosthesis support arms, such as by impeding the pathway of the support arm screw, to allow repositioning or recapturing of the prosthesis. The user can then choose to release the safety stop button to allow completion of the support arm deployment.

The delivery system can also include a delivery catheter, which can have a two-part prosthesis containment capsule divided into distal and proximal portions. To deploy the prosthesis, the proximal capsule portion can be retracted proximally to release the prosthesis arms, which can engage with the ascending aorta. The distal capsule portion can be advanced distally to release the prosthesis inflow section, which can engage the native leaflets of the heart valve. After deployment, the distal and proximal capsule portions can be returned to their closed, pre-deployment configuration to allow safe removal of the delivery system through the deployed prosthesis.

Without the prosthesis loaded within the capsule, the open capsule sections may not align concentrically after deployment, and can create "open mouth" sections which can damage or snag on the deployed prosthesis. In certain embodiments, the delivery system can include a centering element, which can facilitate guiding the two capsule sections back together and align them concentrically. In certain embodiments, the centering element can be a self-expanding centering frame. During loading and deployment, the center frame can be collapsed under the valve prosthesis. Upon deployment, the centering frame can expand, which can also help disengage the valve prosthesis from the valve retainer. Once the valve prosthesis is deployed, the distal capsule portion can be retracted over the centering frame's tapered distal profile to align it concentrically with the proximal capsule portion. The proximal capsule portion can then be advanced over the centering frame's tapered proximal profile to concentrically align it with the distal capsule portion.

In certain embodiments, the centering element can be a centering shaft with a tapered distal profile, which can facilitate guiding the two capsule portions together and align them concentrically. During loading and deployment, the centering shaft can be retracted proximally from the valve prosthesis. Once the valve prosthesis is deployed, the centering shaft can be advanced to the proximal face of the valve retainer, which can help disengage the valve prosthesis from the valve retainer. At this point, the distal capsule portion can be retracted over the centering shaft's tapered distal profile to align it concentrically with the proximal capsule portion. The proximal capsule portion can then be advanced over the centering shaft to concentrically align it with the distal capsule portion. The delivery system can then be safely retracted through the deployed valve prosthesis.

FIG. 1 illustrates delivery system 100, according to an embodiment. Delivery system 100 can include handle 200 and catheter 300. Handle 200 can include front grip 210, rear grip 212, valve release knob 202, support arm knob 204, safety stop button 206, handle decoupling button 208, and decoupling portion 209. Catheter 300 can include outer shaft 302 and capsule 304. Capsule 304 can include proximal capsule portion 306, distal capsule portion 308, intermediate shaft 310, valve containment sleeve 312, and capsule tip 314.

In certain embodiments, valve containment sleeve 312 can be a cylindrical polymer sleeve, configured to retain a heart valve prosthesis within capsule 304. In certain embodiments, capsule tip 314 can be an atraumatic tip to prevent damage to the body lumen as delivery system 100 is advanced through the body. In certain embodiments, capsule tip 314 can include an opening at its distal end to allow delivery system 100 to pass over a guide wire. In certain embodiments, capsule tip 314 can be radiopaque to facilitate locating delivery system 100 within the body using medical imaging.

Figure 2A:
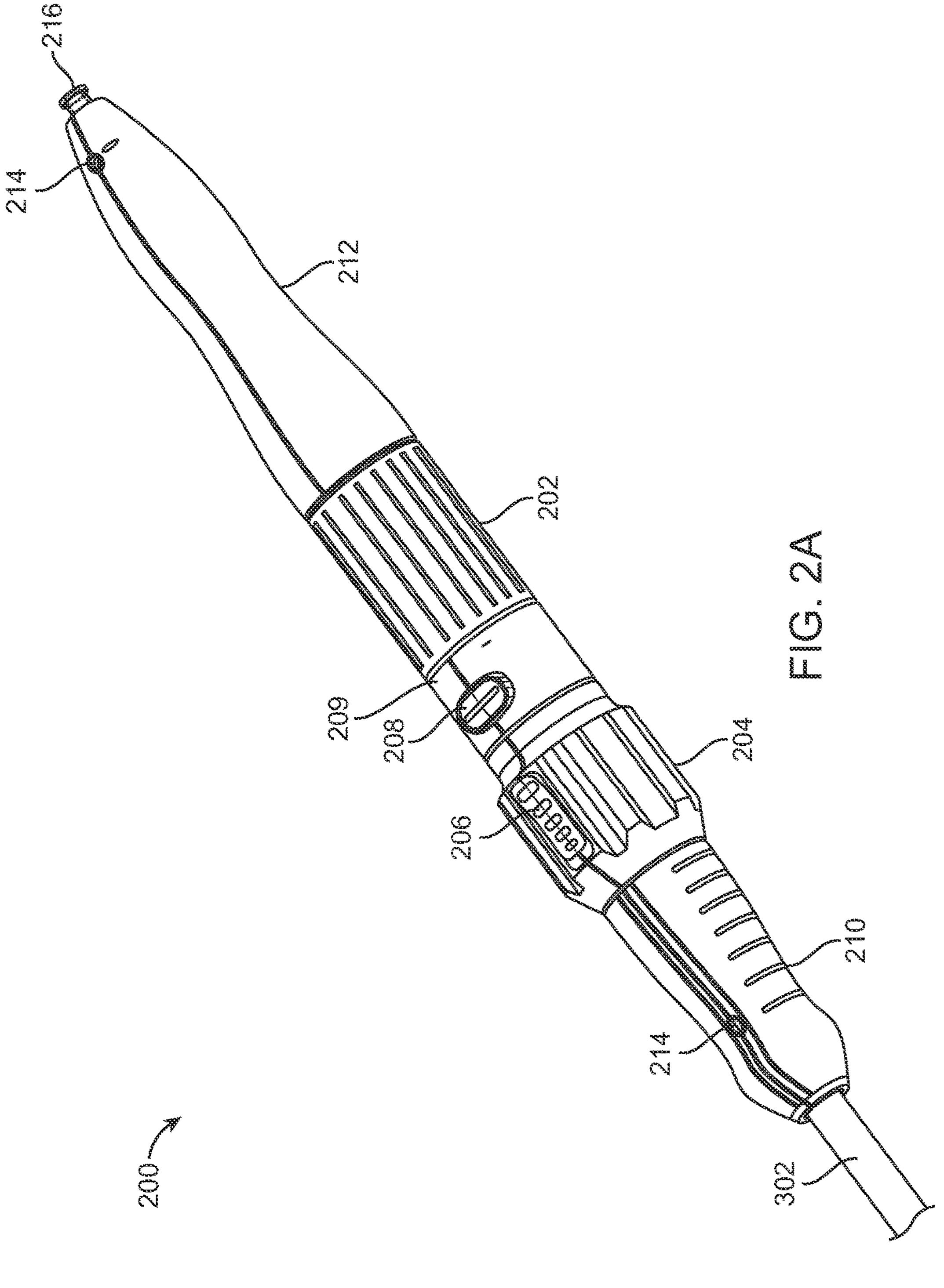
FIG. 2A shows a close-up view of the handle, according to an embodiment.
Figure 2B:
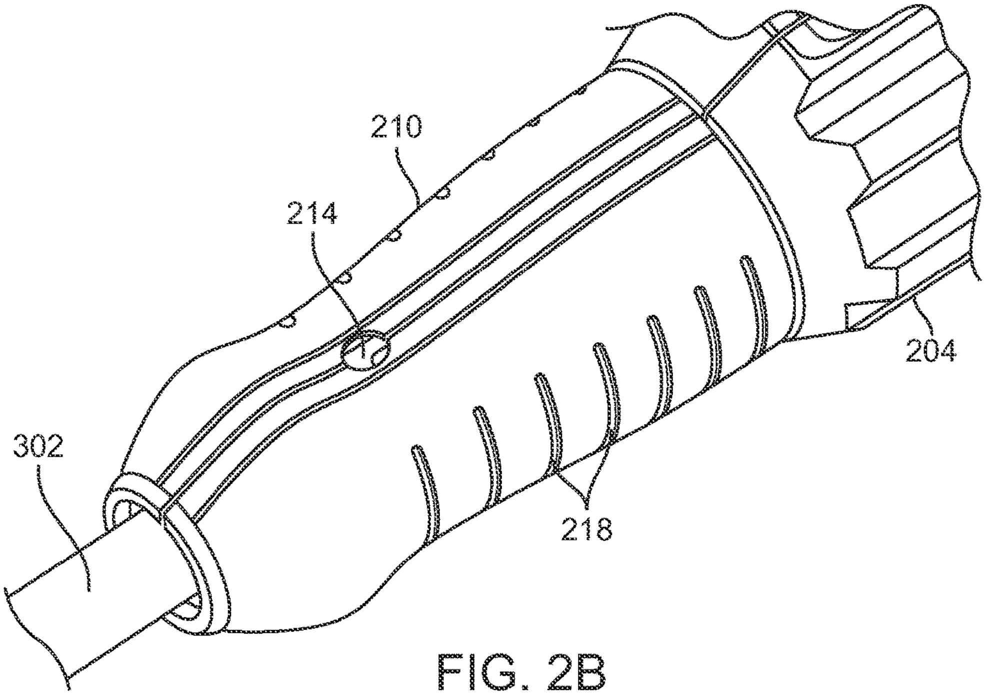
FIG. 2B shows a close-up view of the front grip, according to an embodiment.
Figure 2C:
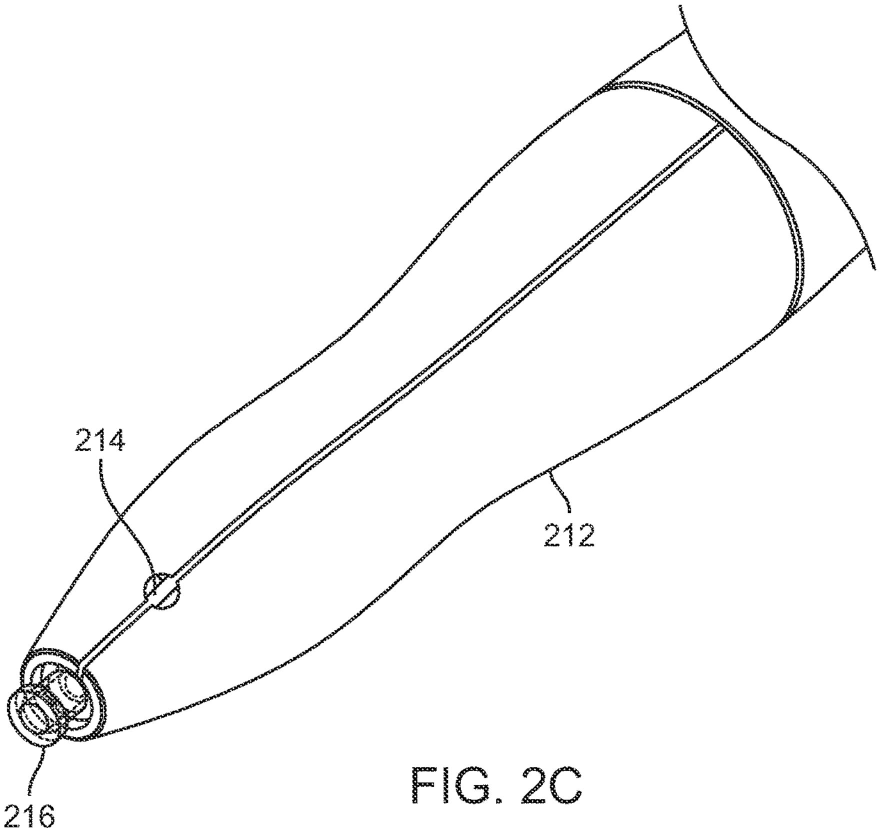
FIG. 2C shows a close-up view of the rear grip, according to an embodiment.

FIGS. 2A-2C illustrate close-up views of handle 200, according to an embodiment. Handle 200 can include front grip 210 and rear grip 212. Front grip 210 and rear grip 212 can be ergonomically designed to facilitate grasping of handle 200 by the user. Front grip 210 and rear grip 212 can be made of a moldable material, such as plastic or rubber, which can provide a smooth and frictional gripping surface. Front grip 210 and rear grip 212 can include grip flush ports 214, which can be used, for example, to remove air or add fluid to delivery system 100. Rear grip 212 can also include end flush port 216, which can also be used for these purposes, and additionally for inserting surgical tools through handle 200. As shown in FIG. 2B, front grip 210 (and/or rear grip 212) can include grooves 218 to further facilitate gripping handle 200.

Handle 200 can also include support arm knob 204, valve release knob 202, safety stop button 206, and handle decoupling button 208. These features can be used to deploy the valve prosthesis and rejoin the capsule portions after deployment, and will be described in further detail below.

Figure 3A:
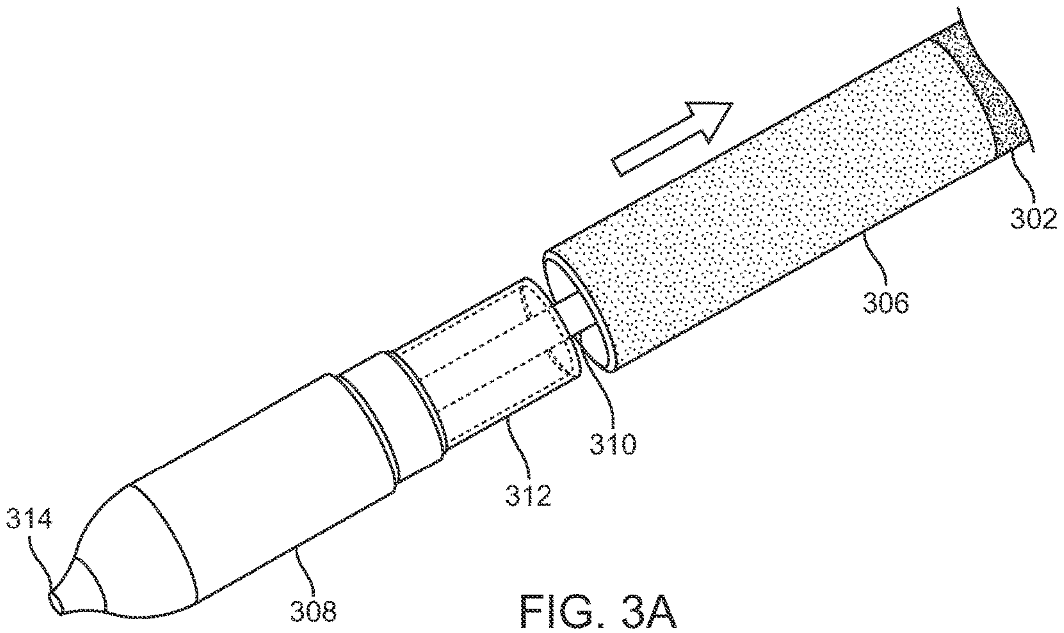
FIGS. 3A-3D illustrate the valve deployment sequence, according to an embodiment.

FIGS. 3A-3D illustrate the deployment and retraction sequence for the valve prosthesis contained within capsule 304, according to an embodiment. FIG. 3A illustrates the initial retraction of outer shaft 302 and proximal capsule portion 306, as indicated by the arrow. Proximal capsule portion 306 can be retracted in the proximal direction, for example, by rotating support arm knob 204. It is understood that the term support arm knob is exemplary. By support arm knob, the disclosure includes knobs, slides, switches and other similar structures that can be activated to cause proximal capsule portion 306 to move axially.

A safety stop feature can be located on handle 200, for example, within support arm knob 204, and can prevent proximal retraction of proximal capsule portion 306 beyond a predetermined distance. The safety stop feature can permit only partial deployment of the valve prosthesis support arms. Medical imaging can be used to determine the location of the support arms, and, if not in the proper location, the valve prosthesis can be repositioned or recaptured. Once in the proper deployment location, the user can activate safety stop button 206 on support arm knob 204 to allow further proximal retraction of proximal capsule portion 306, as indicated by the arrow in FIG. 3B. It is understood that reference to the safety stop button is exemplary, and not meant to be limiting. The safety stop button can be a button, switch, knob, or other similar structures that can prevent proximal retraction of proximal capsule portion 306.

Figure 3B:
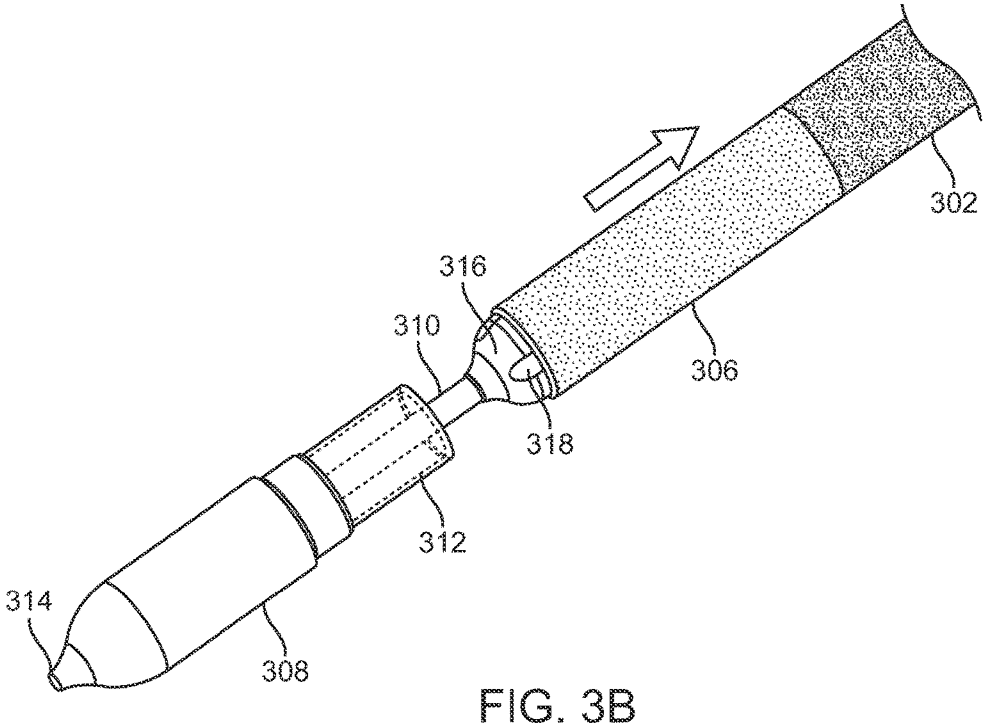

FIG. 3B illustrates capsule 304 with proximal capsule portion 306 in a fully retracted position. In this fully retracted position, proximal dome 316, which can be located at a proximal end of intermediate shaft 310, can be exposed. Proximal dome 316 can facilitate mating of proximal capsule portion 306 and distal capsule portion 308. Proximal dome 316 can include flushing slots 318, which can deliver a flushing fluid to the distal end of catheter 300. In certain embodiments, intermediate shaft 310 shown in FIG. 3B can be stationary relative to outer shaft 302 and inner shaft 320.

Figure 3C:
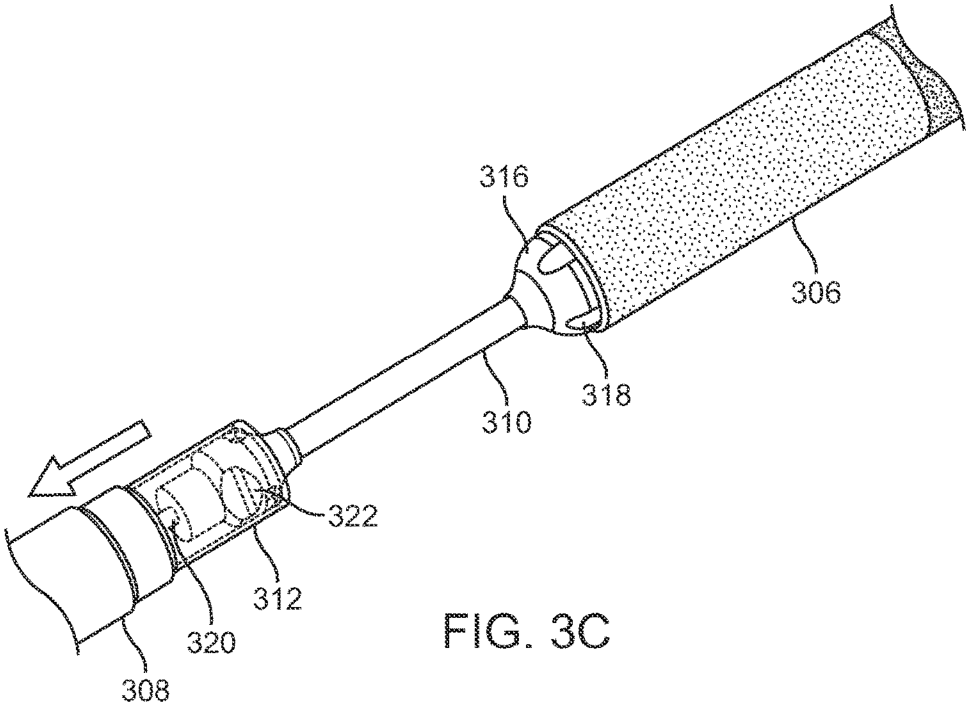

At the stage of deployment illustrated in FIG. 3B, valve containment sleeve 312 can still contain the inflow section of the valve prosthesis. FIG. 3C illustrates advancement of distal capsule portion 308 in the distal direction, as indicated by the arrow. Distal capsule portion 308 can be advanced distally, such as by rotating valve release knob 202. It is understood that the term valve release knob is exemplary. By valve release knob, the disclosure includes knobs, slides, switches and other similar structures that can be activated to cause distal capsule portion 308 to move axially.

Valve release knob 202 can control inner shaft 320, which, in certain embodiments, can move within an interior lumen of intermediate shaft 310, and can be connected to distal capsule portion 308. By advancing distal capsule portion 308, and thus valve containment sleeve 312, in the distal direction, valve retainer 322 can be exposed, thus releasing the valve prosthesis. Valve containment sleeve 312 can form a frictional interference fit with valve retainer 322, which can prevent distal capsule portion 308 from advancing too far in the distal direction.

Figure 3D:
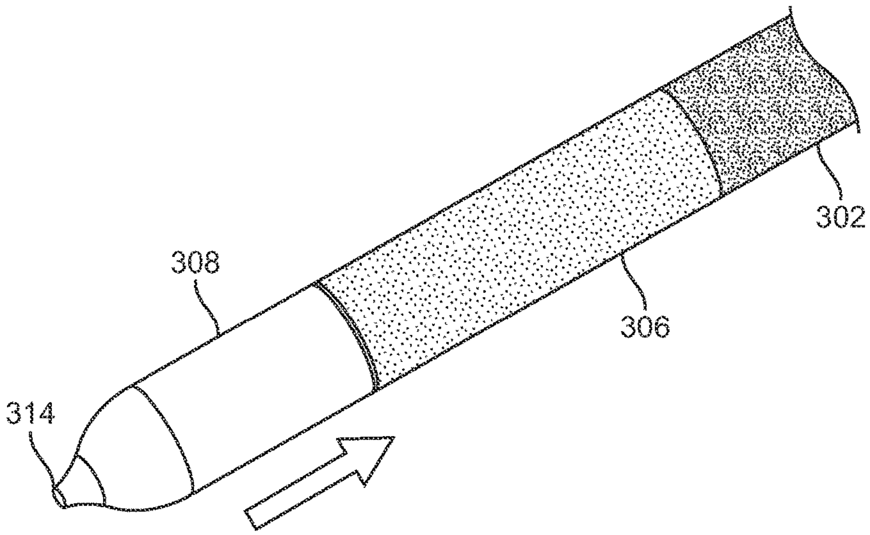

FIG. 3D illustrates proximal retraction of distal capsule portion 308. Manual retraction of distal capsule portion 308 can be performed, for example, by rotating valve release knob 202 in a direction opposite to the direction that advances distal capsule portion 308. Manual retraction of distal capsule portion 308 can also be performed by pressing handle decoupling button 208, which can decouple decoupling portion 209 of handle 200. The user can then pull decoupling portion 209 of handle 200 proximally. This movement can pull inner shaft 320, which can be connected to distal capsule portion 308, in the proximal direction, thus retracting distal capsule portion 308 proximally to mate with proximal capsule portion 306. Once capsule 304 is closed, delivery system 100 can be safely retracted through the deployed valve prosthesis and removed from the body.

Figure 4A:
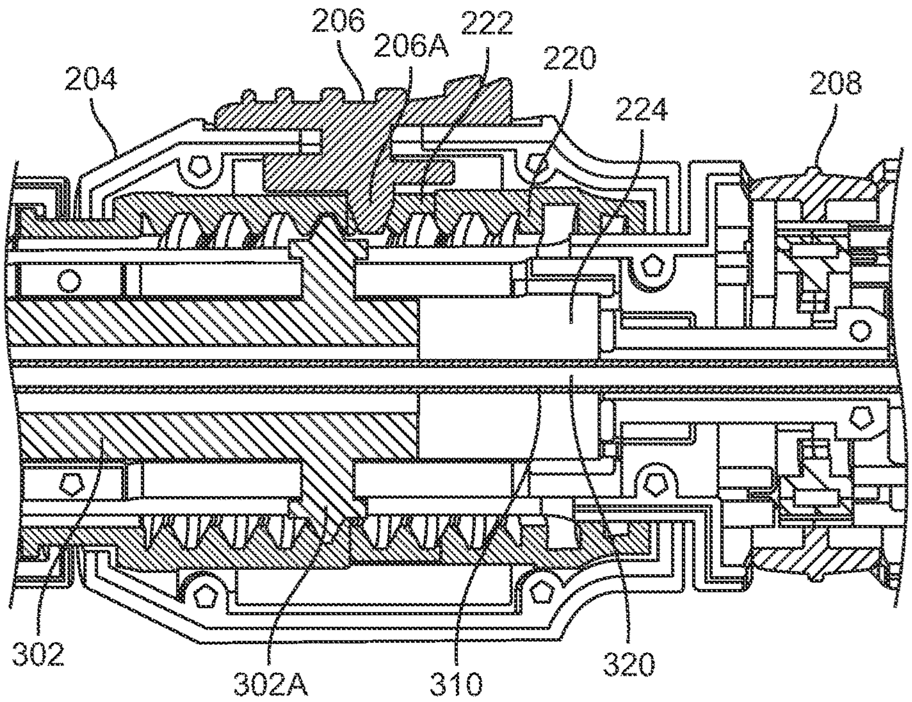
FIGS. 4A-4B illustrate an interior view of the handle, according to an embodiment.
Figure 4B:
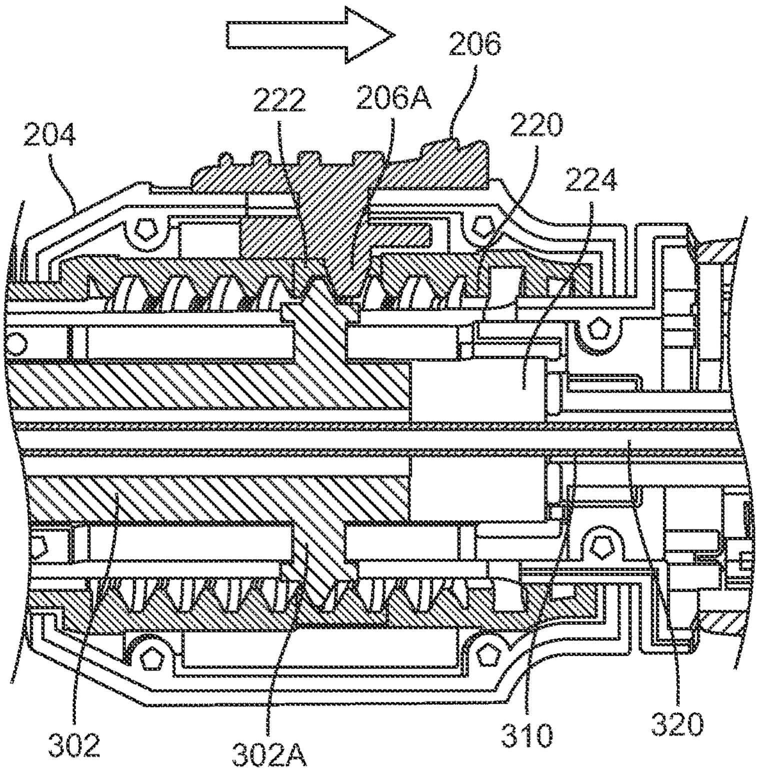

FIGS. 4A and 4B illustrate an interior view of support arm knob 204 and the safety stop mechanism, according to an embodiment. By way of example, as the user rotates support arm knob 204, screw engager 302A of outer shaft 302 can engage support arm deployment screw 220. Generally, safety stop button 206 can be in a spring-loaded safety position, as shown in FIG. 4A. Once screw engager 302A reaches stopper 206A of safety stop button 206, outer shaft 302 is prevented from being retracted further in the proximal direction. At this point, the support arms of the valve prosthesis are partially deployed, and can be repositioned or recaptured, if necessary. Once the valve prosthesis is in the proper location, the user can slide safety stop button 206 in the proximal direction, which can move stopper 206A proximally within slot 222. Outer shaft 302 can then be further retracted within handle lumen 224 in the proximal direction to fully deploy the support arms of the valve prosthesis.

Figure 5A:
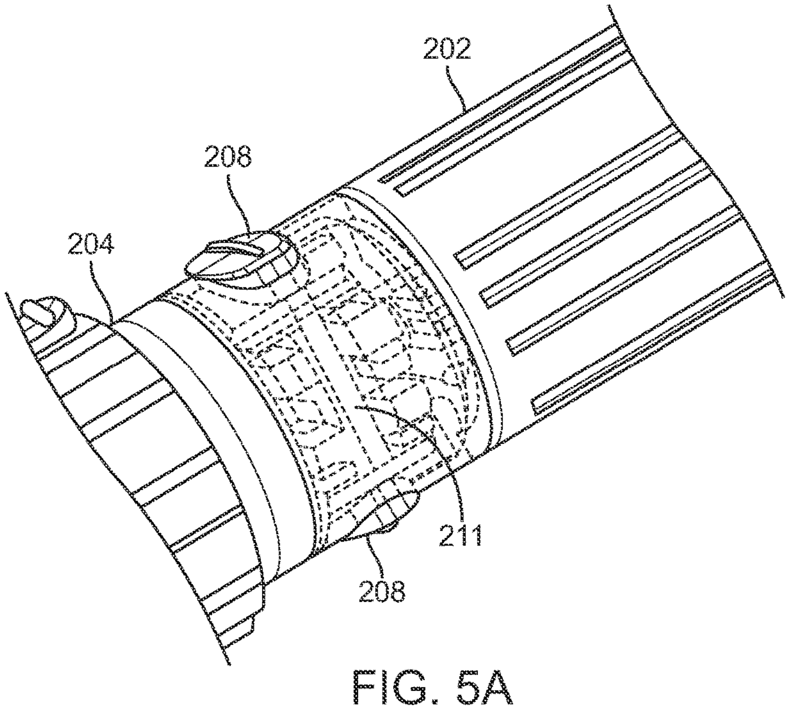
FIG. 5A illustrates a partial interior view of the housing for the decoupling mechanism, according to an embodiment.
Figure 5B:
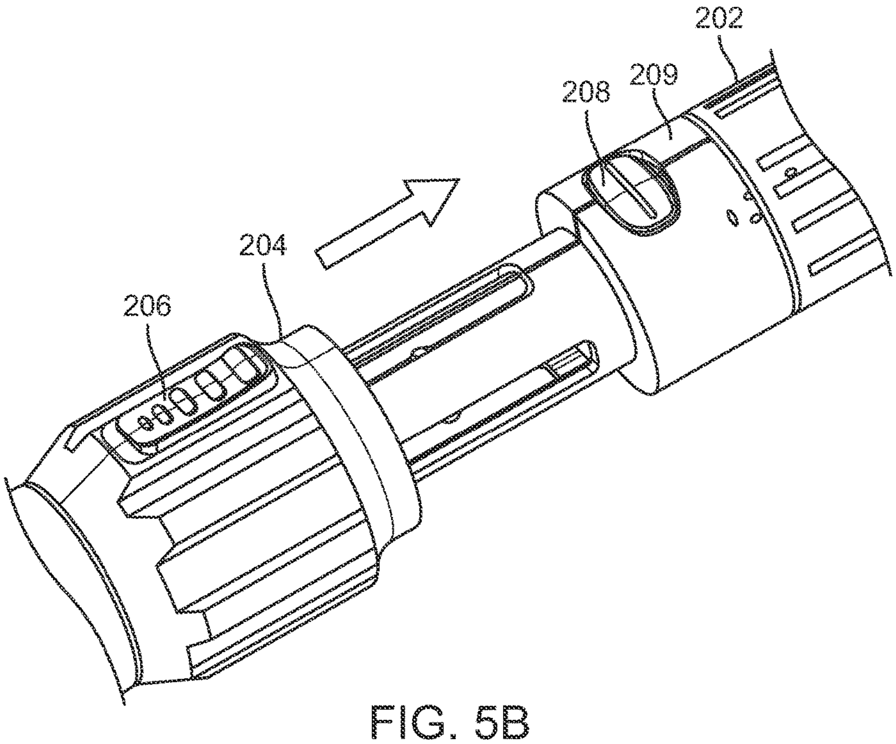
FIG. 5B illustrates the handle after being decoupled, according to an embodiment.

FIGS. 5A and 5B illustrate the decoupling mechanism, according to an embodiment. FIG. 5A shows a partial interior view of handle decoupling portion 209. The handle decoupling mechanism can include one or more handle decoupling buttons 208, which can include coupling elements 211. It is understood that the term handle decoupling buttons is exemplary. By handle decoupling buttons, the disclosure includes knobs, slides, switches and other similar structures that can be activated to allow decoupling of a proximal portion of handle 200. In certain embodiments, coupling elements 211 can engage a counterpart of support arm knob 204 to keep support arm knob 204 and handle decoupling portion 209 together during deployment of the valve prosthesis. Once the valve prosthesis is deployed, the user can press handle decoupling buttons 208, which can decouple coupling elements 211, and allow handle decoupling portion 209 and the rest of the proximal portion of handle 200 to be retracted rapidly in the proximal direction. This movement occur manually, whereby the user pulls handle 200 in the proximal direction. This can retract inner shaft 320, and therefore distal capsule portion 308, in the proximal direction to mate with proximal capsule portion 306 and close capsule 304.

Figure 6A:
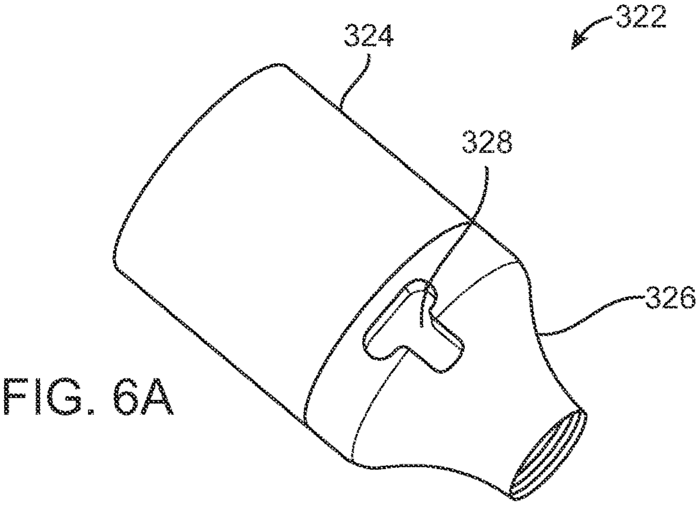
FIGS. 6A-6C illustrate close-up views of the valve retainer, according to certain embodiments.
Figure 6B:
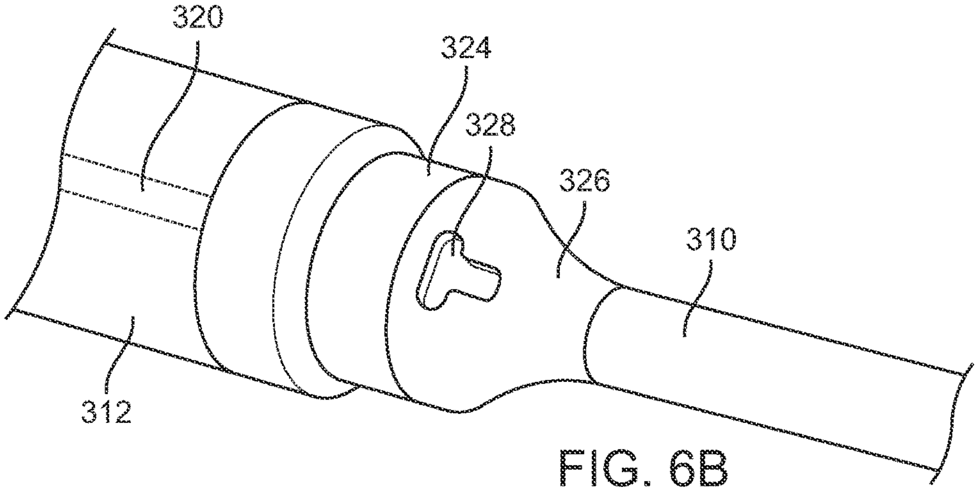

FIGS. 6A and 6B illustrate a close-up view of valve retainer 322, according to an embodiment. Valve retainer 322 can include landing zone 324, retaining portion 326 and one or more valve notch 328. In certain embodiments, portions of valve retainer 322 can be radiopaque, which can facilitate locating the delivery system using medical imaging. As illustrated in FIG. 6B, valve retainer 322 can be connected to the distal end of intermediate shaft 310. Valve notch 328 can be either cut into the surface of retaining portion 326 or raised on the surface of retaining portion 326. Valve notch 328 can correspond to a feature on the valve prosthesis to retain the valve prosthesis within capsule 304 until deployment. Landing zone 324 can be a smooth cylindrical surface located at the distal end of valve retainer 322. Landing zone 324 can prevent prosthesis flaring when engaged with the capsule, and can eliminate hang up points. As inner shaft 320 is advanced in the distal direction to deploy the inflow part of the valve prosthesis from within distal capsule portion 308, valve containment sleeve 312 can ride up on landing zone 324. An interference fit can be created between valve containment sleeve 312 and landing zone 324 of valve retainer 322. This can prevent distal capsule portion 308 from advancing too far in the distal direction during deployment of the valve prosthesis. In certain embodiments, landing zone 324 can be made of a low durometer polymer or rubber and retaining portion 326 can be made of metal, such as stainless steel.

Figure 6C:
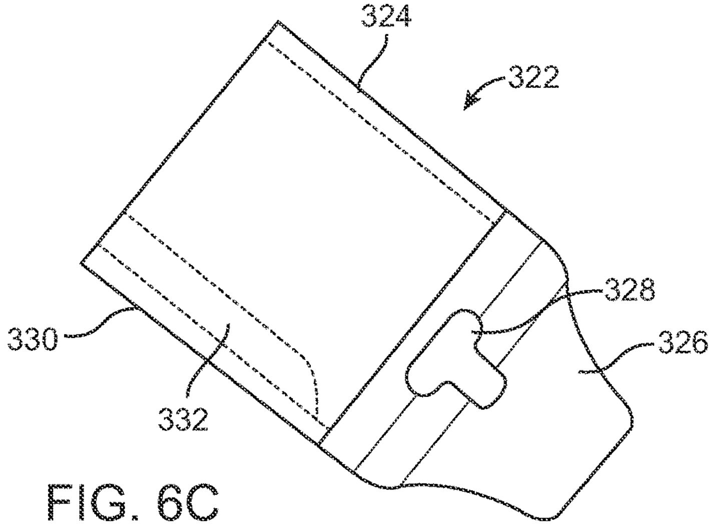

FIG. 6C illustrates a close-up view of valve retainer 322, according to another embodiment. Valve retainer 322 can be made from metal which has a notch, indentation and/or a mark on the side of landing zone 324, such as notch 332. Notch 332 can facilitate positioning of the delivery catheter under fluoroscopy by providing a differentiating appearance to aid with accurate deployment of the prosthesis. In certain embodiments, landing zone 324 can be configured to accommodate notch 332 and allow it to be covered by polymer sleeve 330 to cover the gap created by notch 332 to maintain proper fit between valve retainer 322 and capsule 304. Polymer sleeve 330 can be non-radiopaque, thus allowing valve retainer 322 to have features to facilitate accurate positioning while maintaining a round profile for a smooth fit with capsule 304 and for a smooth edge for retracting valve retainer 322 through the prosthesis after deployment.

Figure 7A:
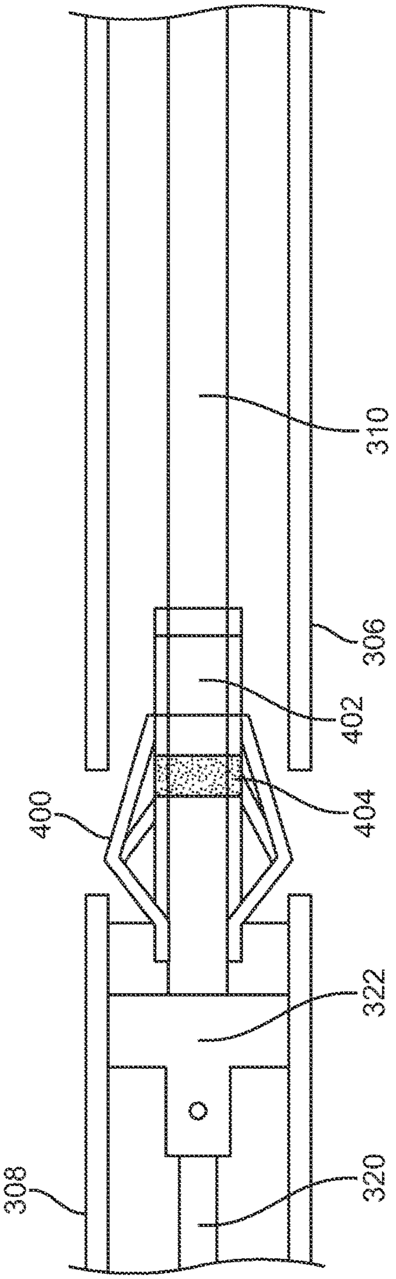
FIGS. 7A-7B illustrate the centering frame attached to the delivery system and separately, according to an embodiment.
Figure 7B:
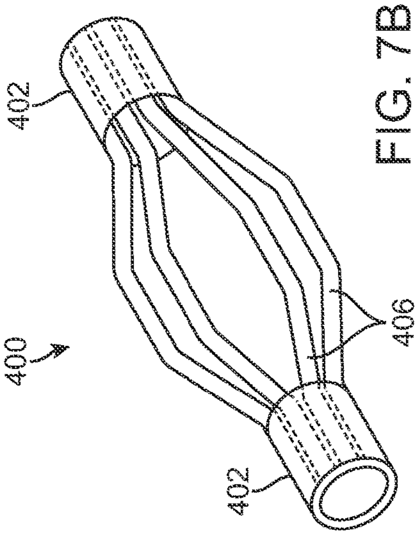

FIGS. 7A and 7B illustrate a capsule centering element, according to an embodiment. In certain embodiments, the capsule centering element can be centering frame 400. Centering frame 400 can be connected to intermediate shaft 310, such as by attachment ring 402, which can be located at either a proximal or distal end of centering frame 400. Attachment ring 402 can be crimped about intermediate shaft 310 to secure centering frame 400 to intermediate shaft 310. Centering frame 400 can be made of a self-expanding shape memory alloy, such as nitinol. In certain embodiments, centering frame 400 can be made from a laser-cut metal tube. In certain embodiments, centering frame 400 can be made of a plurality of wires 406, such as nitinol wires, welded to attachment ring 402. In certain embodiments, centering frame 400 can include radiopaque marker 404, which can facilitate positioning the valve prosthesis and aligning distal capsule portion 308 and proximal capsule portion 306 using medical imaging.

When the valve prosthesis is loaded in capsule 304, self-expanding centering frame 400 can be collapsed under the valve prosthesis. When the valve prosthesis is deployed, centering frame 400 can expand to provide a lead in for distal capsule portion 308 to mate with proximal capsule portion 306. The expansion of centering frame 400 can also facilitate disengaging the valve prosthesis from valve retainer 322. In certain embodiments, centering frame 400 can be coated with a biocompatible lubricant to facilitate guiding distal capsule portion 308 and proximal capsule portion 306 back together. In certain embodiments, centering frame 400 can at least partially recollapse as distal capsule portion 308 and proximal capsule portion 306 slide over centering frame 400 and back together.

Figure 8A:
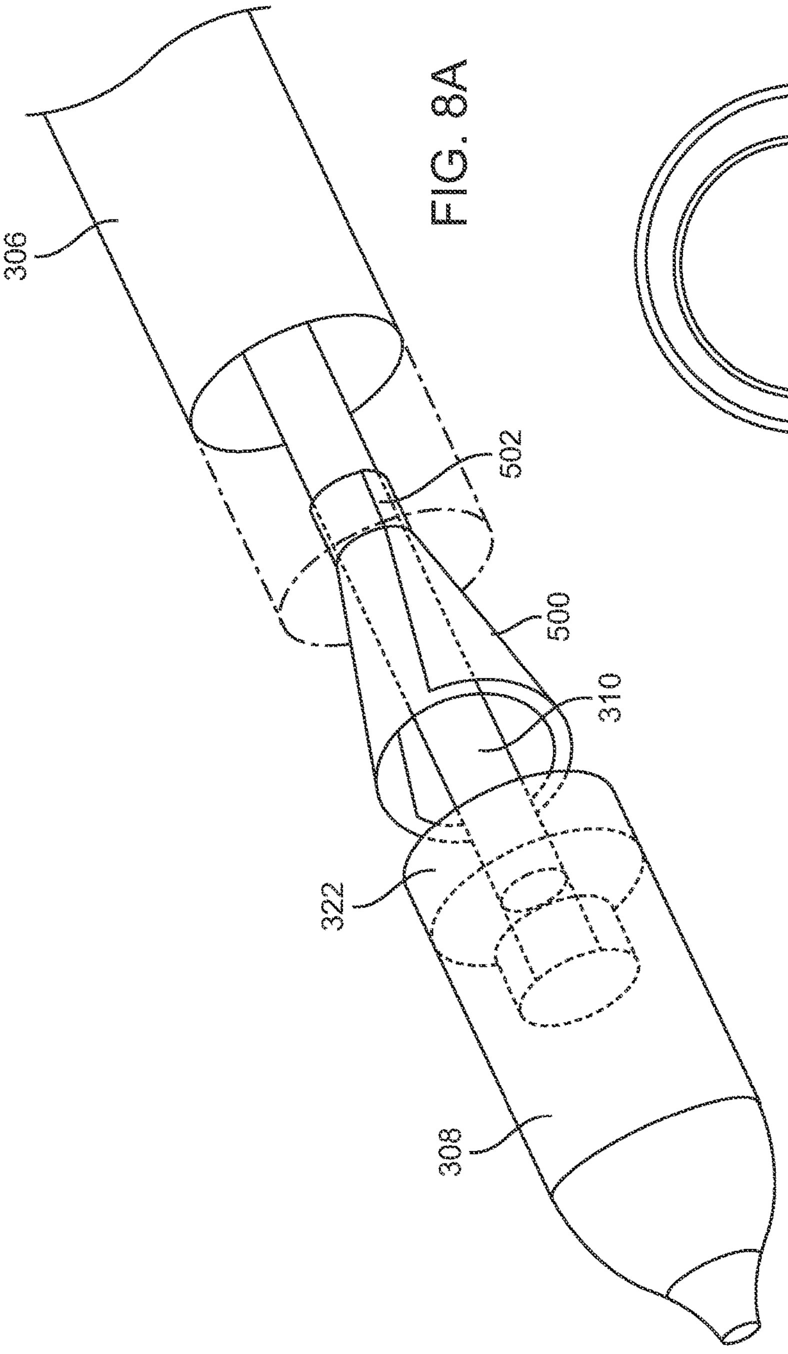
FIGS. 8A-8B illustrate the centering funnel attached to the delivery system and separately, according to an embodiment.
Figure 8B:
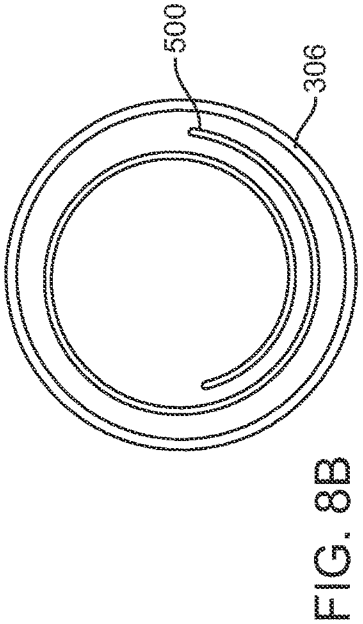

As illustrated in FIGS. 8A and 8B, in certain embodiments, the capsule centering element can be centering funnel 500. Centering funnel 500 can be connected to intermediate shaft 310, such as by attachment ring 502, which can be located at either a proximal or distal end of centering funnel 500. Centering funnel 500 can be made of a self-expanding shape memory alloy, such as nitinol. In certain embodiments, as illustrated, for example, in FIG. 8B, centering funnel 500 can be a nitinol sheet rolled into a funnel or spring shape. In certain embodiments, centering funnel 500 can be constrained within an elastomeric sleeve, which can expand with centering funnel 500. FIG. 8B provides a view along a longitudinal axis of delivery system 100, showing centering funnel 500 coiled within proximal capsule portion 306 prior to delivery of the valve prosthesis. Generally, the expanded diameter of centering funnel 500 can be less than or equal to the diameter of distal capsule portion 308 and proximal capsule portion 306. In certain embodiments, proximal capsule portion 306 can be guided distally over centering funnel 500 to mate with distal capsule portion 308. In certain embodiments, distal capsule portion 308 can be pulled proximally over and around centering funnel 500 to mate with proximal capsule portion 306.

Once the valve prosthesis is deployed, centering funnel 500 can expand in diameter, thus creating a funnel shape to provide a guide for distal capsule portion 308 to mate with proximal capsule portion 306. In certain embodiments, centering funnel 500 can be manually expanded, such as by balloon inflation. In certain embodiments, centering funnel 500 can be coated with a biocompatible lubricant to facilitate guiding distal capsule portion 308 and proximal capsule portion 306 back together. In certain embodiments, centering funnel 500 can at least partially recollapse as distal capsule portion 308 and proximal capsule portion 306 slide over centering funnel 500 and back together.

In certain embodiments, the capsule centering element can be structures such as, but not limited to, a cell-like stent structure or a braided cylinder, attached to intermediate shaft 310 by attachment ring 402 at one or more end.

Figure 9A:
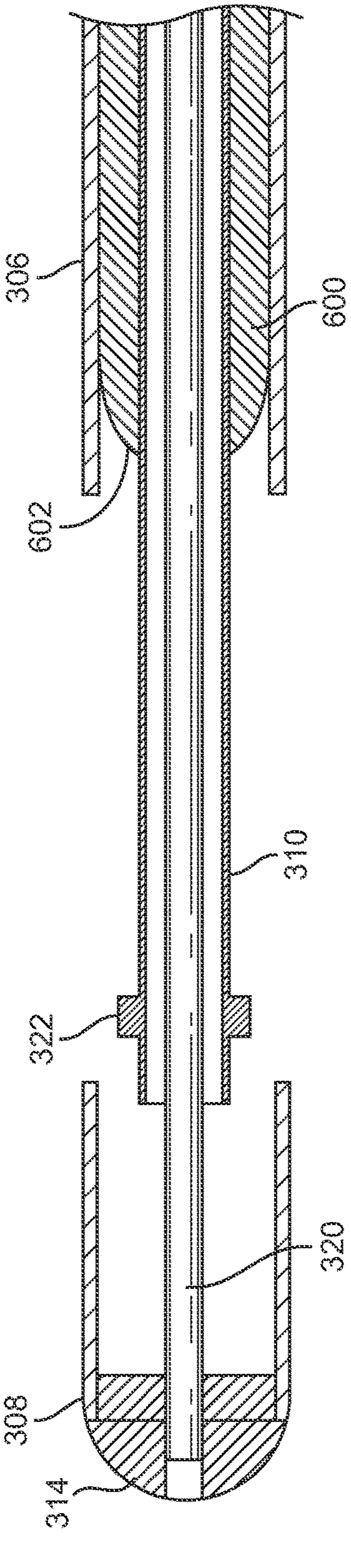
FIGS. 9A-9B illustrate the centering shaft, according to an embodiment.
Figure 9B:
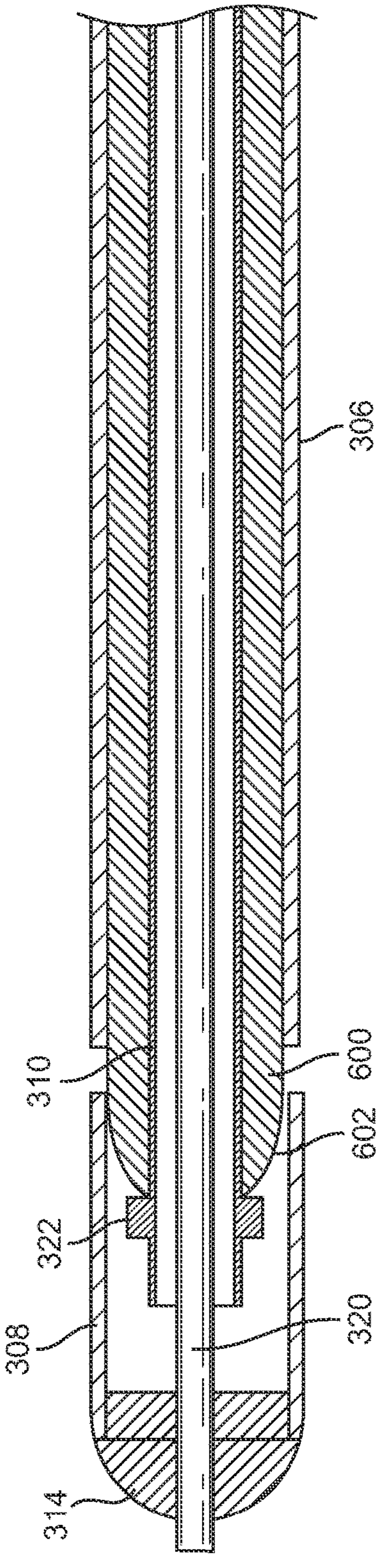
Figure 10A:
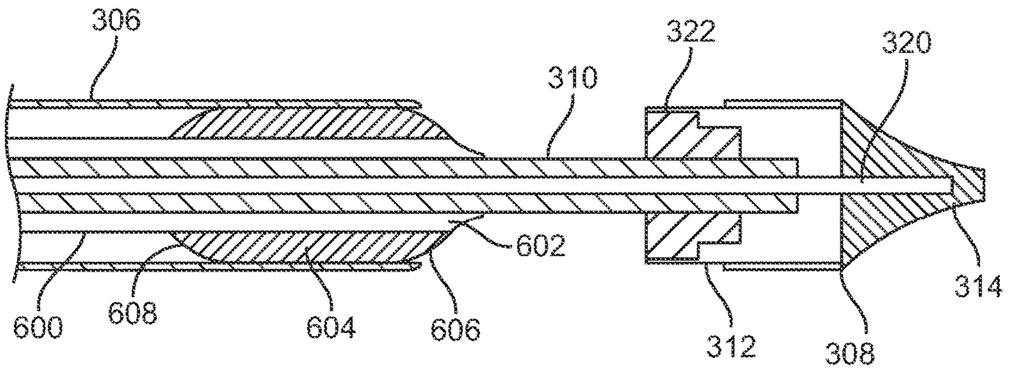
FIGS. 10A-10B illustrate the centering shaft including a centering dome, according to an embodiment.
Figure 10B:
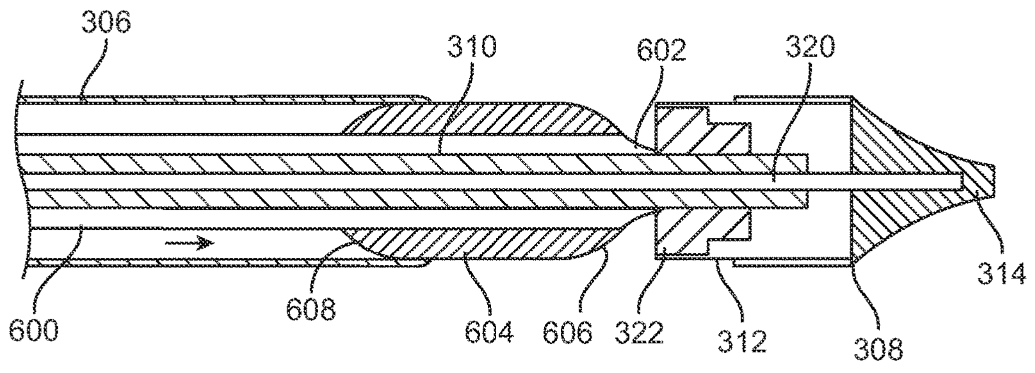

As illustrated in FIGS. 9A and 9B, as well as FIGS. 10A and 10B, in certain embodiments, the capsule centering element can be centering shaft 600. Centering shaft 600 can be, for example, a polymer or composite shaft that can slide independently along intermediate shaft 310. Centering shaft 600 can be retracted proximately to allow the valve prosthesis to be loaded within capsule 304 prior to the valve replacement procedure. In certain embodiments, centering shaft 600 can have a continuous proximal profile and tapered tip 602, which can facilitate mating of distal capsule portion 308 with proximal capsule portion 306. After the valve prosthesis is deployed, centering shaft 600 can be advanced distally out of proximal capsule portion 306. Centering shaft 600 can be advanced to the proximal face of valve retainer 322 to facilitate disengaging the valve prosthesis from valve retainer 322. Distal capsule portion 308 can then be retracted proximally, such as by rotating valve release knob 202 to retract inner shaft 320 in the proximal direction. Distal capsule portion 308 can slide over tapered tip 602 of centering shaft 600. Proximal capsule portion 306 can also be advanced distally to concentrically mate proximal capsule portion 306 with distal capsule portion 308. In certain embodiments, centering shaft 600 can be coated with a biocompatible lubricant to facilitate guiding distal capsule portion 308 and proximal capsule portion 306 back together. In certain embodiments, proximal retraction of distal capsule portion 306 can be performed by activating handle decoupling button 208.

As illustrated in FIGS. 10A and 10B, in certain embodiments, centering shaft 600 can include centering dome 604. Centering dome 604 can include distal taper 606 and proximal taper 608. In the embodiments shown in FIGS. 10A and 10B, centering shaft 600 can operate in a mechanistically similar manner as in FIGS. 9A and 9B. After distal capsule portion 308 is advanced distally to deploy the valve prosthesis, centering shaft 600 can be advanced distally up to valve retainer 322 to facilitate disengaging the valve prosthesis from valve retainer 322. Distal capsule portion 308 can be retracted proximally such that distal capsule portion 308 and valve containment sleeve 312 slide over distal taper 606 of centering dome 604. Proximal capsule portion 306 can be advanced in the distal direction over proximal taper 608 of centering dome 604 to mate with distal capsule portion 308. In certain embodiments, proximal retraction of distal capsule portion 306 can be performed by activating handle decoupling button 208.

Methods of delivering a heart valve prosthesis are also disclosed. References to the figures are made by way of example, and are not meant to be limiting. Prior to the procedure, the desired valve implantation location should be determined. This can be done with the assistance of medical imaging, such as a CT scan. For trans-aortic prosthetic aortic valve implantation, the implantation location can generally be located within the aortic sinus such that the distal part of the heart valve prosthesis engages the leaflets of the native aortic valve, and the proximal part of the heart valve prosthesis engages the inner wall of the ascending aorta. Alternative implantation sites can be used, and the optimal implantation site can be determined for each individual patient.

Generally, for a trans-aortic procedure, the chest can be prepared and the ascending aorta can be accessed, such as by a mini-sternotomy or a thoracotomy. In certain embodiments, the user can place delivery system 100 over a guide wire and advance delivery system 100 through the ascending aorta. In certain embodiments, medical imaging can be used to locate features of delivery system 100 to facilitate positioning of delivery system 100 at the desired deployment location.

Once in the desired anatomical position, the user can, for example, rotate support arm knob 204 to retract outer shaft 302, and therefore proximal capsule portion 306, to partially release the valve support arms. If the support arms are not in the desired deployment location, the valve prosthesis can be repositioned or recaptured. Once the user verifies that the support arms are correctly positioned, proximal capsule portion 306 can be fully retracted. In certain embodiments, this can be accomplished by pressing safety stop button 206 and further rotating support arm knob 204. The user can then advance distal capsule portion 308, for example, by rotating valve release knob 202. Once the valve prosthesis is fully deployed, the user can activate handle decoupling button 208 to initiate rapid closure of capsule 304. The user can then retract delivery system 100 through the deployed valve prosthesis and remove it from the body. The user can then close the incision by standard clinical techniques.

In certain embodiments, after distally advancing distal capsule portion 308 to deploy the valve prosthesis, the user can advance centering shaft 600 in the distal direction. Distal capsule portion 308 can then be retracted proximally over tapered tip 602 of centering shaft 600. Proximal capsule portion 306 can be advanced distally to mate proximal capsule portion 306 with distal capsule portion 308. In certain embodiments, a self-expanding capsule centering element can expand after deployment of the valve prosthesis. The capsule centering element can help guide distal capsule portion 308 and proximal capsule portion 306 back together.

The foregoing description has been presented for purposes of illustration and description. It is not intended to be exhaustive or to limit the precise embodiments disclosed. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. A prosthesis delivery system comprising:
a handle assembly comprising:
  a first control mechanism; and
  a second control mechanism;
a delivery catheter extending from the handle assembly, the delivery catheter comprising:
  an outer shaft controlled by the first control mechanism;
  a prosthesis containing capsule comprising:
    a proximal capsule portion connected to the outer shaft; and
    a distal capsule portion releasably coupled to the proximal capsule portion comprising:
      a distal tip; and
      a prosthesis containment sleeve;

an intermediate shaft, having a prosthesis retainer located at a distal end;

an inner shaft controlled by the second control mechanism and connected to the distal capsule portion; and a centering element attached to the intermediate shaft, the centering element located proximally from the prosthesis retainer and having a collapsed configuration and an expanded configuration configured to guide the distal capsule portion and the proximal capsule portion together when closing the prosthesis containing capsule; and a heart valve prosthesis located within the prosthesis containing capsule in a radially collapsed configuration, wherein with the heart valve prosthesis located within the prosthesis containing capsule, the centering element is in the collapsed configuration under the heart valve prosthesis.

2. The prosthesis delivery system of claim 1, further comprising a safety mechanism connected to the first control mechanism, and configured to prevent proximal retraction of the outer shaft beyond a predetermined distance.

3. The prosthesis delivery system of claim 1, wherein the prosthesis retainer comprises a proximal portion connected to the intermediate shaft, and a distal portion configured to create a compressible interference fit with the prosthesis containment sleeve.

4. The prosthesis delivery system of claim 1, wherein the intermediate shaft is stationary such that the centering element is longitudinally stationary in the collapsed configuration and the expanded configuration.

5. The prosthesis delivery system of claim 1, wherein the first and second control mechanisms are rotatable control knobs.

6. The prosthesis delivery system of claim 1, wherein the centering element comprises a self-expanding frame attached to the intermediate shaft at either a proximal end or a distal end of the frame.

7. The prosthesis delivery system of claim 6, wherein the self-expanding frame comprises a shape memory alloy.

8. The prosthesis delivery system of claim 6, wherein the self-expanding frame comprises a plurality of nitinol wires.

9. The prosthesis delivery system of claim 1, wherein the heart valve prosthesis is self-expanding.

10. The prosthesis delivery system of claim 1, wherein the handle assembly further comprises a decoupling mechanism configured to decouple a decoupling portion of the handle assembly from a remainder of the handle assembly such that the decoupling portion may be translated proximally to move the inner shaft proximally.

* * * * *